United States Patent [19]
Blumenfeld et al.

[11] Patent Number: 5,387,506
[45] Date of Patent: Feb. 7, 1995

[54] USE OF GENETIC MARKERS TO DIAGNOSE FAMILIAL DYSAUTONOMIA

[75] Inventors: Anat Blumenfeld, Brookline; James F. Gusella, Framingham, both of Mass.

[73] Assignee: The General Hospital Corporation, Boston, Mass.

[21] Appl. No.: 890,719

[22] Filed: May 29, 1992

[51] Int. Cl.⁶ .......................... C12Q 1/68; C12P 19/34
[52] U.S. Cl. ........................ 435/6; 435/912; 935/77; 935/78
[58] Field of Search .................... 435/6, 91, 91.2; 935/77, 78, 64; 536/23.1, 23.5, 24.3

[56] References Cited
PUBLICATIONS

Kwiatkowski et al Genomics (Jan. 1992) 12:229–240.
Lathrop et al Genomics (1988) 3:361–366.
Proceedings of the 8th International Congress of Human Genetics, Washington, D.C., USA, Oct. 6–11, 1991. AM J Hum Genet 49 (4 Suppl.). 1991. 336. Coden: AJHGAG ISSN: 0002–9297 6—(C) File Biosis Blumenfeld A. et al. "Advances in Linkage Analysis in Familial Dysautonomia."
Blumenfeld A. et al. "Linkage Analysis in Familial Dysautonomia", Bonne-Tamir, B. and A. Adam (Ed.). Genetic Diversity Among Jews: Diseases and Markers of the DNA Level; Goodman's International Conference, Israel, Jun. 1990. XXVIII+460P. Oxford University Press: New York, N.Y., USA; Oxford, England, UK. Illus. M.

*Primary Examiner*—Margaret Parr
*Assistant Examiner*—Carla Myers
*Attorney, Agent, or Firm*—Morgan & Finnegan

[57] ABSTRACT

The familial dysautonomia gene is identified as located on the long arm of human chromosome 9. As a result of this localization, the presence of the familial dysautonomia gene in a subject of a family with an affected individual is detected by analyzing human chromosome 9 of the subject for a DNA sequence containing the familial dysautonomia gene on the long arm of human chromosome 9 located between D9S59 and D9S127.

16 Claims, 3 Drawing Sheets

Lod Scores Between Dysautonomia and Chromosome 9 Markers

| Marker | Recombination Value | | | | | | $\hat{\theta}$ | $\hat{z}$ |
|--------|------|------|------|------|------|------|------|------|
|        | 0.00 | 0.05 | 0.10 | 0.20 | 0.30 | 0.40 |      |      |
| D9S15  | -∞   | -5.54 | -1.76 | 0.53 | 0.76 | 0.36 | 0.266 | 0.81 |
| D9S109 | -∞   | 5.54 | 5.42 | 3.85 | 2.04 | 0.60 | 0.066 | 5.62 |
| D9S29  | -∞   | 5.56 | 5.35 | 3.82 | 2.04 | 0.60 | 0.063 | 5.59 |
| D9S127 | -∞   | 8.01 | 7.21 | 4.82 | 2.44 | 0.68 | 0.040 | 8.05 |
| D9S58  | 18.48 | 15.93 | 13.39 | 8.47 | 4.22 | 1.23 | 0.000 | 18.48 |
| D9S59  | -∞   | 6.08 | 6.05 | 4.39 | 2.36 | 0.74 | 0.070 | 6.21 |
| HXB    | -∞   | 5.99 | 5.89 | 4.27 | 2.30 | 0.70 | 0.068 | 5.91 |
| GSN    | -∞   | 6.09 | 6.39 | 4.79 | 2.62 | 0.83 | 0.085 | 6.45 |
| ASS    | -∞   | -5.07 | -1.64 | 0.41 | 0.55 | 0.20 | 0.303 | 0.56 |

FIG. I

Lod Scores Between Dysautonomia and Chromosome 9 Markers

| Marker | Recombination Value | | | | | | | $\hat{\theta}$ | $\hat{Z}$ |
|---|---|---|---|---|---|---|---|---|---|
| | 0.00 | 0.05 | 0.10 | 0.20 | 0.30 | 0.40 | | | |
| D9S15 | -∞ | -5.54 | -1.76 | 0.53 | 0.76 | 0.36 | | 0.266 | 0.81 |
| D9S109 | -∞ | 5.54 | 5.42 | 3.85 | 2.04 | 0.60 | | 0.066 | 5.62 |
| D9S29 | -∞ | 5.56 | 5.35 | 3.82 | 2.04 | 0.60 | | 0.063 | 5.59 |
| D9S127 | -∞ | 8.01 | 7.21 | 4.82 | 2.44 | 0.68 | | 0.040 | 8.05 |
| D9S58 | 18.48 | 15.93 | 13.39 | 8.47 | 4.22 | 1.23 | | 0.000 | 18.48 |
| D9S59 | -∞ | 6.08 | 6.05 | 4.39 | 2.36 | 0.74 | | 0.070 | 6.21 |
| HXB | -∞ | 5.99 | 5.89 | 4.27 | 2.30 | 0.70 | | 0.068 | 5.91 |
| GSN | -∞ | 6.09 | 6.39 | 4.79 | 2.62 | 0.83 | | 0.085 | 6.45 |
| ASS | -∞ | -5.07 | -1.64 | 0.41 | 0.55 | 0.20 | | 0.303 | 0.56 |

FIG. 2

USE OF GENETIC MARKERS TO DIAGNOSE FAMILIAL DYSAUTONOMIA

STATEMENT AS TO RIGHTS TO INVENTION

The present invention was developed at Massachusetts General Hospital under obligation to assign the invention to the same. The Dysautonomia Foundation has an option for an exclusive license for the present invention.

FIELD OF THE INVENTION

The invention relates to genetic testing; more specifically, to a method of detecting the presence of the familial dysautonomia gene and also to identification of the location of familial dysautonomia in the genome.

BACKGROUND OF THE INVENTION

Familial dysautonomia, or the Riley-Day syndrome, is a rare inherited neurological disease affecting the development and survival of sensory, sympathetic and some parasympathetic neurons (Riley, C. M., et al., *Pediatrics*, 1949;3:468–477; Axelrod, F. B., et al., *Am. J. Dis. Child*, 1984;138:947–954; Axelrod, F. B., *Cell Molec. Biol. Neuronal Dev.*, Ed.: Black, 1.B., Plenum Press, NY; 1984, 331–340). It is the most common and the best known of a group of rare disorders, termed congenital sensory neuropathies, that are characterized by widespread sensory, and variable autonomic dysfunction. Patients with familial dysautonomia are affected from birth with a variety of symptoms such as decreased sensitivity to pain and temperature, vomiting crises and cardiovascular instability all of which might result from a deficiency in a neuronal growth factor pathway (Breakefield, X. O., etal., *Proc. Natl. Acad. Sci. USA*, 1984;81:4213–4215; Breakefield, X. O., et al., *Mol. Biol. Med.*, 1986; 3:483–494). Neuropathological findings have clearly differentiated familial dysautonomia from other congenital sensory neuropathies (Axelrod, F. B., et al., *Am. J. Dis. Child*, supra, Axelrod, F. B., *Cell Molec. Biol, Neuronal Dev.*, supra.) The disorder is inherited as an autosomal recessive with complete penetrance and is currently confined to individuals of Ashkenazi Jewish descent (Brunt, P. W., et al., *Medicine*, 1970;49:343–374). In this population, the estimated carrier frequency is 1 in 30 with a disease incidence of 1 in 3600 births (Maayan, C., et al., *Clinical Genet.*, 1987;32:106–108). The clear-cut pattern of transmission, apparent restriction to one ethnic population and lack of confounding phenocopies suggest that all cases of familial dysautonomia might have descended from a single mutation (Axelrod, F. B., et al., *Am. J. Dis. Child*, supra, Axelrod, F. B., *Cell Molec, Biol, Neuronal Dev*, supra).

For more than 40 years, familial dysautonomia related research concentrated on biochemical, physiological and histological-pathological aspects of the disorder. Although those studies contributed to a better understanding of the nature of the disease, and indicated that a deficiency in a neuronal growth factor pathway might be the cause of familial dysautonomia, they did not result in identification of the familial dysautonomia gene, thus, those studies did not contribute to the availability of a genetic test for familial dysautonomia.

Chromosomal localization of the gene causing familial dysautonomia can facilitate genetic counseling and prenatal diagnosis in affected families. Subsequent delineation of closely linked markers which show strong linkage disequilibrium with the disorder and ultimately, identification of the defective gene can allow screening of the entire at-risk population to identify carriers, and potentially reduce the incidence of new cases.

Linkage analysis can be used to find the location of a gene causing a hereditary disorder and does not require any knowledge of the biochemical nature of the disease, i.e. the mutated protein that is believed to cause the disease. Traditional approaches depend on assumptions concerning the disease process that might implicate a known protein as a candidate to be evaluated. The genetic localization approach using linkage analysis can be used to first find the general chromosomal region in which the defective gene is located and then to gradually reduce the size of the region in order to determine the location of the specific mutated gene as precisely as possible. After the gene itself is discovered within the candidate region, the messenger RNA and the protein are identified and along with the DNA, are checked for mutations.

This latter approach has practical implications since the location of the disease can be used for prenatal diagnosis even before the altered gene that causes the disease is found. Linkage analysis can enable families from caucasian origin, even many of those that did not have a sick child, to know whether they were carriers of a disease gene and to evaluate the condition of an unborn child through molecular diagnosis.

The transmission of a disease within families, then, can be used to find the defective gene. This approach to molecular etiology is especially useful in studies of inherited neurologic disorders, as only several thousand of the hundred-or-so thousand genes active in the nervous system are known, and nervous tissue is hard to obtain for biochemical analysis.

Linkage analysis is possible because of the nature of inheritance of chromosomes from parents to offspring. During meiosis the two homologues pair to guide their proper separation to daughter cells. While they are lined up and paired, the two homologues exchange pieces of the chromosomes, in an event called "crossing over" or "recombination". The resulting chromosomes are chimeric, that is, they contain parts that originate from both parental homologues. The closer together two sequences are on the chromosome, the less likely that a recombination event will occur between them, and the more closely linked they are. In a linkage analysis experiment, two positions on the chromosomes are followed from one generation to the next to determine the frequency of recombination between them. In a study of an inherited disease, one of the chromosomal positions is marked by the disease gene or its normal counterpart, i.e. the inheritance of the chromosomal region can be determined by examining whether the individual displays symptoms of the disorder or not. The other position is marked by a DNA sequence that shows natural variation in the population such that the two homologues can be distinguished based on the copy of the "marker" sequence that they possess. In every family, the inheritance of the genetic marker sequence is compared to the inheritance of the disease state. If within a family carrying a recessive disorder such as familial dysautonomia every affected individual carries the same form of the marker and all the unaffected individuals carry at least one different form of the marker, there is a great probability that the disease gene and the marker are located close to each other. In this way, chromosomes may be systematically checked with known markers and compared to the disease state. The data obtained from the different families is combined, and analyzed together by a computer using statistical methods. The result is information indicating the probability of linkage between the genetic marker and the disease allowing different distances between them. A positive result can mean that the disease is very close to the marker, while a negative result indicates that it is far away on that chromosome, or on an entirely different chromosome.

Linkage analysis is performed by typing all members of the affected family at a given marker locus and evaluating the co-inheritance of a particular disease state with the marker probe, thereby determining whether the two of them are close to each other in the genome. The recombination frequency can be used as a measure of the genetic distance between two gene loci. A recombination frequency of 1% is equivalent to 1 map unit, or 1 centiMorgan (cM), which is roughly equivalent to 1,000 kb of DNA. This relationship holds up to frequencies of about 20% (or 20 cM).

The entire human genome is 3,300 cM long. In order to find an unknown disease gene within 5-10 CM of a marker locus, the whole human genome can be searched with 165-330 informative marker loci spaced at 5-10 CM intervals (Botstein, D. R. L., et at., *Am. J. Hum. Genet.*, 1980; 32:314-331.) The reliability of linkage results is established by using a number of statistical methods.

The method most commonly used for the analysis of linkage in humans is the LOD score method, developed by Morton, 1955; and incorporated into the computer program LIPED by Ott, 1976. Lod scores are the logarithm of the ratio of the likelihood that two loci are linked at a given distance to that they are not linked (>50 cM apart). The advantage of using logarithmic values is that they can be summed among families with the same disease. This becomes necessary given the relatively small size of human families.

By convention, a total lod score greater than +3.0 (that is, odds of linkage at the specified recombination frequency being 1000 times greater than odds of no linkage) is considered to be significant evidence for linkage at that particular recombination frequency; a total lod score of less than −2.0 (that is, odds of no linkage being 100 times greater than odds of linkage at the specified frequency) is considered to be strong evidence that the two loci under consideration are not linked at that particular recombination frequency.

Until recently, most linkage analyses have been performed on the basis of twopoint data; that is, the relationship between the disorder under consideration and a particular genetic marker. However, as a result of the rapid advances in mapping the human genome over the last few years, and concomitant improvements in computer methodology, it has become feasible to carry out linkage analyses using multipoint data; that is, a simultaneous analysis of linkage between the disease and several linked genetic markers, when the recombination distance among the markers is known.

Multipoint analysis is advantageous for two reasons. First, the informativeness of the pedigree is usually increased. Each pedigree has a certain amount of potential information, dependent on the number of parents heterozygous for the marker loci and the number of affected individuals in the family. However, few markers are sufficiently polymorphic as to be informative in all those individuals. If multiple markers are considered simultaneously, then the probability of an individual being heterozygous for at least one of the markers is greatly increased. Second, an indication of the position of the disease gene among the markers may be determined. This allows identification of flanking markers, and thus eventually allows isolation of a small region in which the disease gene resides. Lathrop, G. M., et at., *Proc Natl. Acad. Sci. USA,* 1984;81:3443-3446 have written the most widely used computer package, LINKAGE, for multipoint analysis.

When two loci are extremely close together, recombination between them is very rare. In fact, the rate at which the two neighboring loci recombine can be so slow as to be unobservable except over many generations. The resulting allelic association is generally referred to as linkage disequilibrium. Linkage disequilibrium is defined as specific alleles at two loci that are observed together on a chromosome more often than expected from their frequencies in the population. Such results are strongly influenced by founder and subpopulation effects, so it is generally necessary to examine data only within one ethnic group or population isolate, which is the case for familial dysautonomia, which is only found in individuals of Ashkenazi Jewish descent. Linkage disequilibrium is usually used to further define the chromosomal region containing the disease gene, once linkage has been demonstrated in a specific region. When disequilibrium is suspected, the affected individuals are checked for increased frequency of homozygosity for the marker loci, since these persons have two copies of the disease gene. An excess of homozygosity for one allele, as measured against general population frequencies (using the $X^2$ statistic) would indicate linkage disequilibrium. The major advantage of disequilibrium study over standard linkage analysis is the need to test only a single affected individual per family, which is the usual case with rare recessive disorders, thus increasing the population amenable for analysis.

The marker locus must be very tightly linked to the disease locus in order for linkage disequilibrium to exist. Potentially, markers within a few cM of the disease gene could be examined and no linkage disequilibrium detected. Linkage disequilibrium has been observed with markers within 500 kb of the cystic fibrosis gene (Kerem, et al., 1989), *science* 245:1073-1080. If linkage is found with several marker loci that are spaced along several centiMorgans, and none of them show recombination between the marker tested and the disease status in affected families, disequilibrium is the only genetic approach that can narrow down the chromosomal region linked to the disease gene.

A specific DNA sequence in an individual can undergo many different changes, such as deletion of a sequence of DNA, insertion of a sequence that was duplicated, inversion of a sequence, or conversion of a single nucleotide to another. Changes in a specific DNA sequence may be traced by using restriction enzymes that recognize specific DNA sequences of 4-6 nucleotides. Restriction enzymes, cut (digest) the DNA at their specific recognized sequence, resulting in one million or so pieces. When a difference exists that changes a sequence recognized by a restriction enzyme to one not recognized, the piece of DNA produced by cutting the region will be of a different size. The various possible fragment sizes from a given region therefore depend on the precise sequence of DNA in the region. Variation in the fragments produced is termed "restriction fragment length polymorphism" (RFLP). The different sized-fragments reflecting different variant DNA sequences can be visualized by separating the digested DNA according to its size on an agarose gel and visualizing the individual fragments by annealing to a radioactively labeled, DNA "probe". Each individual can carry two different forms of the specific sequence. When the two homologues carry the same form of the polymorphism, one band will be seen. More than two forms of a polymorphism may exist for a specific DNA marker in the population, but in one family just four forms are possible; two from each parent. Each child inherits one form of the polymorphism from each parent. Thus, the origin of each chromosome region can be traced (maternal or paternal origin).

RFLPs have proven to be somewhat limiting in that they usually give only two alleles at a locus and not all parents are heterozygous for these alleles and thus informative for linkage. Newer methods take advantage of the presence of DNA sequences that are repeated in tandem, variable numbers of time and that are scattered throughout the human genome. The first of these described were variable number tandem repeats of core sequences (VNTRs) (Jeffreys, A. J. V., et al., *Nature*, 1985;314:67–73; Nakamura, Y. M., et at., *Science*, 1987;235:1616–1622.) VNTRs are detected using unique sequences of DNA adjacent to the tandem repeat as marker probes, and digesting the DNA with restriction enzymes that do not recognize sites within the core sequence. However, highly informative VNTR loci have not been found on all chromosome arms, and those which have been identified are often situated near telomeres (Royle, et al., 1988), *Genomics* 3:352–360, leaving large regions of the genome out of reach of these multi-allelic marker loci.

Recently, it was discovered that eukaryotic DNA has tandem repeats of very short simple sequences such as $(dC-dA)_n$. $(dG-dT)_n$ where n=10–60 (termed GT repeat). The (dG-dT) repeats occur every 30–60 kb along the genome (Weber, J. L., et at., *Am, J. Hum. Genet.*, 1989;44:388–396; Litt, M., et al., *Am. J. Hum. Genet.*, 1989;44:397–401), and Alu 3' (A)n repeats occur approximately every 5 kb (Economou, 1990), *Proc. Natl. Acad. Sci., USA* 87:2951. Other repeats, such as GA repeats, trinucleotide and tetranucleotide repeats are less common.

Oligonucleotides encoding flanking regions of these repeats are used as primers for the polymerase chain reaction (PCR) (Saiki, 1988, *Science* 239:48–491) on a small sample of DNA. By amplifying the DNA with radioactive mucleotides, the sample may be quickly resolved on a sequencing gel and visualized by autoradiography. Because these polymorphisms are comprised of alleles differing in length by only a few base pairs, they are not detectable by conventional Southern blotting as used in traditional RFLP analysis.

The use of PCR to characterize GT polymorphic markers enables the use of less DNA, typically only ten nanograms of genomic DNA is needed, and is faster than standard RFLP analysis, because it essentially only involves amplification and electrophoresis (Weber, supra).

Consequently, the present invention compromises genetic linkage analysis to identify an individual having the familial dysautonomia gene. In addition, discovery of markers linked to the familial dysautonomia gene will enable researchers to focus future analysis on a small chromosomal region and will accelerate the sequencing of the familial dysautonomia gene.

It is an object of the present invention to locate markers linked to the familial dysautonomia gene and to identify the location of the familial dysautonomia gene in the human genome.

It is a further object of the present invention to provide a genetic test specific for the familial dysautonomia gene.

It is a still further object of the present invention to provide a genetic test to the prenatal diagnosis and carrier detection specific for the familial dysautonomia gene.

SUMMARY OF THE INVENTION

The present invention describes, for the first time, the chromosomal location which carries the gene responsible for familial dysautonomia and provides a method of detecting the presence of a familial dysautonomia gene in a subject. The location by applicants of the familial dysautonomia gene is on the long arm of human chromosome 9 (q arm) more specifically between D9S59 and D9S127. A most probable location of the familial dysautonomia gene is close to D9S58.

Linkage analysis with markers located on the long arm of human chromosome 9 is used to identify the inheritance of the allele causing familial dysautonomia with 80–90% accuracy at the present time.

In particular, the test is carried out by studying the heritability of a combination of two or more polymorphisms linked to familial dysautonomia among any number of suitable family members so as to allow the determination of phenotype. The test can be used prenatally to screen a fetus or presymptomatically, to screen a subject at risk through his/her family.

The invention also extends to products useful for carrying out the assay, such as DNA probes (labelled or unlabelled), kits and the like.

BRIEF DESCRIPTION OF THE DRAWINGS

FIG. 2—Table of lod scores of different chromosome 9 markers in dysautonomia families. The lod scores were calculated assuming conventional recombination values (0) between familial dysautonomia and the marker; 0, 0.05, 0.1, 0.2, 0.3, 0.4. When there is at least one recombination event between a marker tested and the disease, the lod score at $\hat{\Theta}=0$ is minus infinity. At other recombination values, lod scores can be positive or negative. The highest lod score obtained by each marker ($\hat{Z}$), and the recombination value in which that lod score was calculated ($\hat{\Theta}$), are also included. This gives a rough estimation of the genetic distance between the marker and the disease. The markers are ordered according to their location on chromosome 9, when D9S15 is the most centromeric one, and ASS is the closest to the telomere. In some cases, the order of the markers is unknown, because they were not placed on the same genetic map and were not typed with the same pedigrees (D9S109-D9S29-D9S127). In this case the order was determined according to $\hat{\Theta}$.

DESCRIPTION OF THE PREFERRED EMBODIMENTS

The present invention describes, for the first time, the location and chromosomal band which carries the gene responsible for familial dysautonomia.

Figure 1:
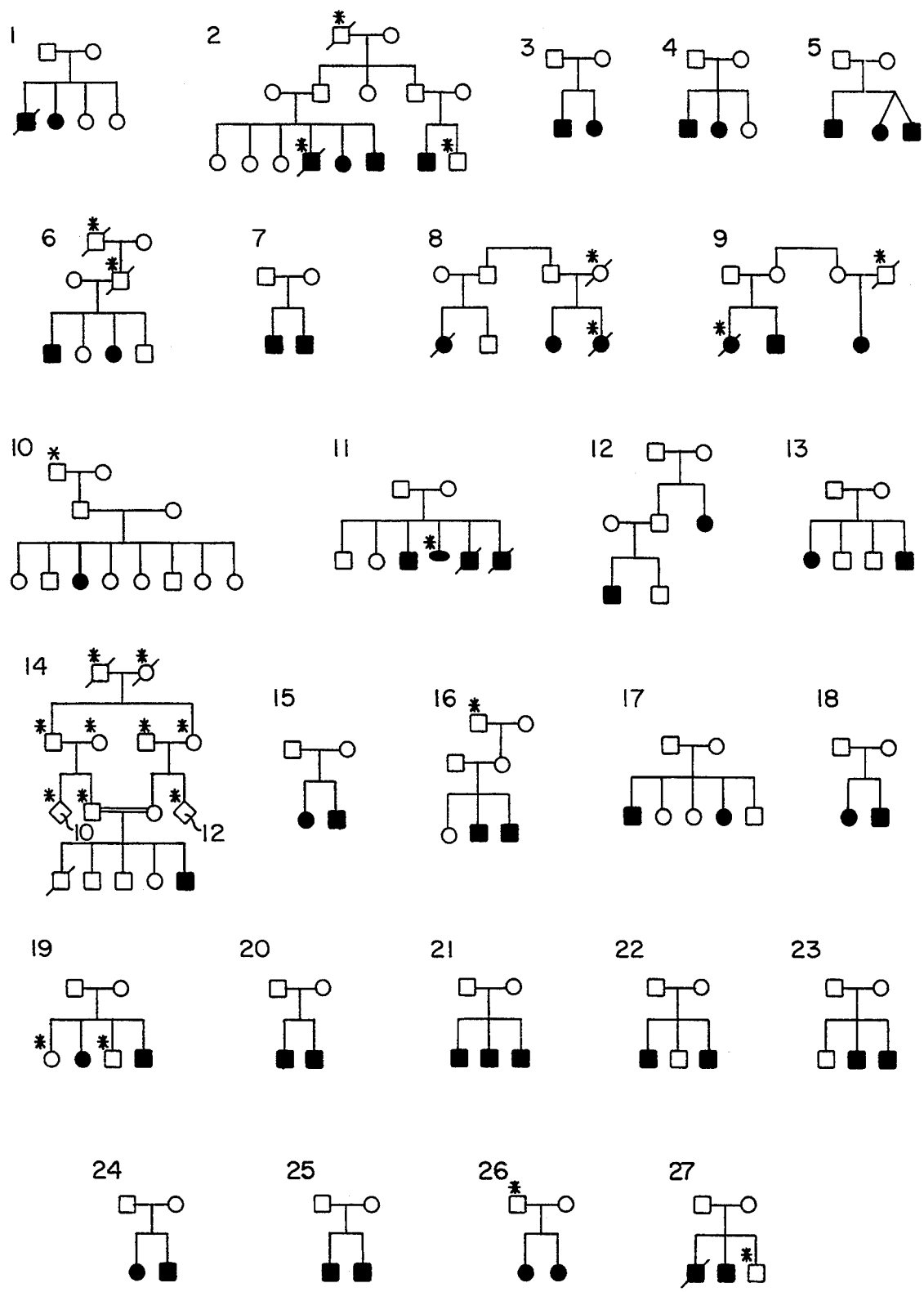
FIG. 1—Pedigrees of twenty-seven families affected with familial dysautonomia; twenty-five were used for linkage analysis. Symbols: empty circle unaffected female; filled circle, affected female; empty square, unaffected male; filled square, affected male; slashed symbol, deceased; star symbol, blood not collected.

To find the chromosomal location of the familial dysautonomia gene, polymorphic markers were typed in 25 families (FIG. 1). All selected families have two or three dysautonomic members (23 families), large .pedigree (one family) or consanguinity between the parents (one family). DNAs from all family members, carriers, affected and unaffected, were tested with each marker. The result of the typing was compared to the disease status of each individual. Linkage analysis computer data management and statistical programs were employed and the lod scores of the different families were pooled together to give the lod score for each marker at different distances from the disease.

Over 250 DNA polymorphisms distributed on all 22 autosomes were checked before linkage was found. Most of the polymorphisms had negative lod score values and, hence, it was possible to exclude chromosomal regions as being possible sites carrying the familial dysautonomia gene. The few that had positive lod scores at some distances from the marker, were slightly positive but far from +3.0, that is conventionally accepted as a minimal demand for linkage. Moreover, those slightly positive markers were surrounded by negative flanking markers, indicating that the familial dysautonomia gene was not in the immediate vicinity of that chromosomal region.

The present invention relates to the location of polymorphic markers on the long arm of human chromosome 9, which are linked to the familial dysautonomia gene and enable linkage analysis to predict both an affected individual having both familial dysautonomia genes and a carrier with only one familial dysautonomia gene. Linkage analysis with these polymorphisms can identify the inheritance of the familial dysautonomia allele with 80-90% accuracy. Polymorphisms are DNA sequences located on the long arm of human chromosome 9. More specifically these polymorphisms are in, or immediately adjacent to the q31 band on the long arm of chromosome 9. The linkage analysis of the invention can be carried out by using any polymorphism linked to the familial dysautonomia allele. The use of the term polymorphism is intended to encompass any marker DNA sequence which is linked to the familial dysautonomia gene. The polymorphism can be a polymorphic repeating sequence or allelic forms of a gene. The polymorphism must be located close to, or be the same as, the familial dysautonomia gene. If located close to the familial dysautonomia gene, the polymorphism must be sufficiently close to the familial dysautonomia gene such that the familial dysautonomia gene and the marker are linked. Linkage may be determined by a significant LOD score or other acceptable statistical linkage determination.

The marker can be detected by a variety of methods. The preferred detection means the use of radioactive nucleotides in PCR amplification of the polymorphism, but other detection methods such as ligase chain reaction (LCR) can also be used. The polymorphism can be detectably labelled by a radioisotope or by chemical modification enabling direct detection of the polymorphism. Flourescent or colorimetric means can also be used. Detection of the polymorphism can be indirect, e.g. a radioactive complementary strand of DNA, resulting from incorporation of radioactive nucleotides in a polymerase chain reaction.

For typing restriction fragment length polymorphisms (RFLPs), genomic DNA prepared from cell lines derived from all members of families affected with familial dysautonomia was digested with restriction endonuclease, resolved by electrophoresis on 0.8% agarose gels and transferred to Hybond N+ membranes. Blots were hybridized with probe DNAs radioactively labeled by random priming and visualized by autoradiography (Ozelius, L., et al., Neuron, 1989;2:1427-1434).

For typing simple sequence repeat polymorphisms, the method described by Weber, Am, J, Hum. Genet., supra, was used with the following modifications; PCR reaction volume was reduced to 10 μl using 5-10 ng genomic DNA, 40 ng of each primer, and about 0.25 U Taq polymerase (Boehringer). In most cases α-$^{32}$P-dGTP (3,000 Ci/mmole, Amersham) was used as the labeled nucleotide. PCR conditions varied as has been previously described for the specific markers. Dried gels were subjected to autoradiography for 4-16 hours using Kodak X-OMAT AR film.

The LIPIN (v. 2.1) data management program was used for entry of marker phenotypes into a VAX8700 computer. Pairwise lod scores were calculated using MLINK (v. 3.5). Autosomal recessive inheritance, complete penetrance, no rate of new mutations, and a gene frequency of 1/60 were assumed for familial dysautonomia.

Figure 3:
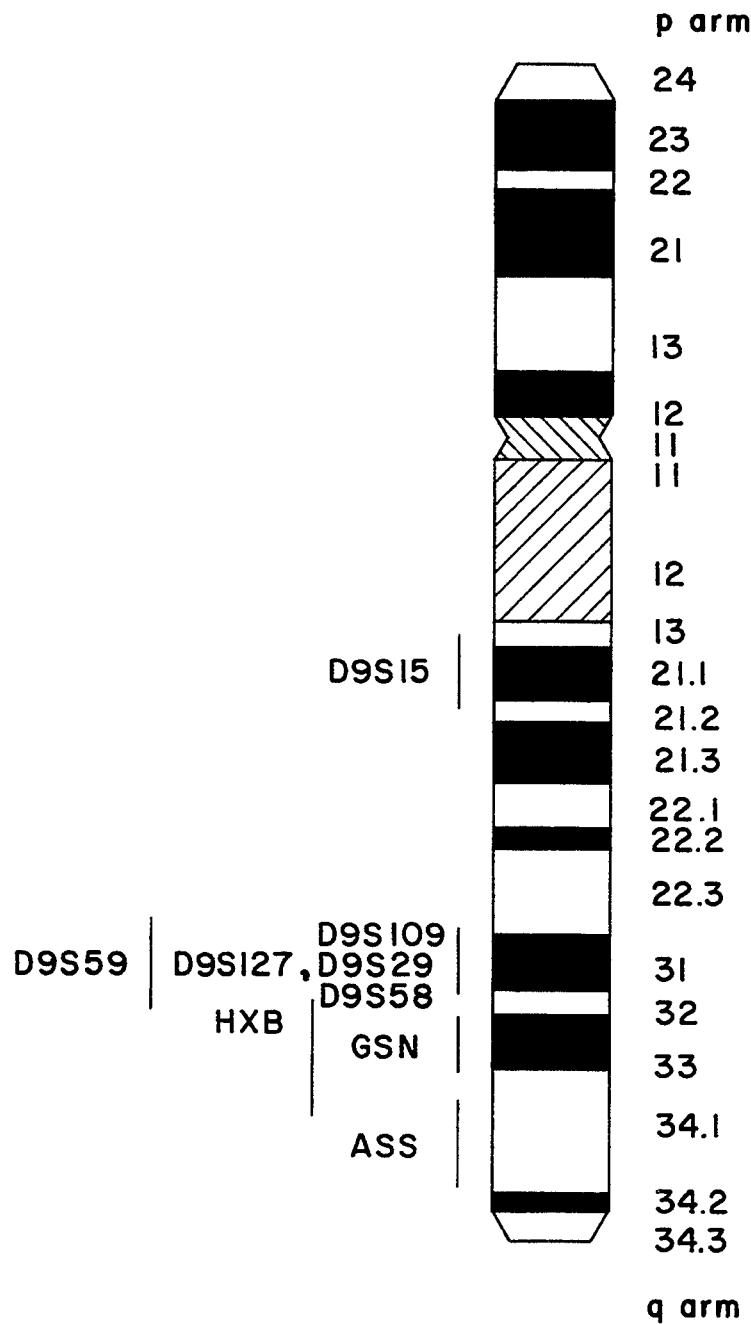
FIG. 3—Physical map of human chromosome 9 markers. The names of the bands on chromosome 9 were determined according to Gimsa dyes. All the markers that show linkage with familial dysautonomia (FIG. 2) are located on the long arm (q arm) of chromosome 9, most of which are on the 31 band.

The first DNA polymorphism that gave a significant positive lod score (FIG. 2) was HXB which is located on the long arm of chromosome 9 (FIG. 3). Table 1 provides the oligonucleotide primer sequences for each polymorphism.

TABLE 1

| Marker | Oligonucleotide Primer Sequence* |
|---|---|
| HXB[1] | ATAGCCAAAGAGAGGTGCCC (SEQ ID NO: 1) |
| | AGAGCCCTTCTGTCTTTTCC (SEQ ID NO: 2) |
| D9S127[2] | CCCTCAAAATTGCTGTCTAT (SEQ ID NO: 3) |
| | AGATTGATTGATACAAGGATTTG (SEQ ID NO: 4) |
| D9S58[3] | CCTGAGTAGCCGGGACTATA (SEQ ID NO: 5) |
| | TAGGCAACACATCAAGATCCT (SEQ ID NO: 6) |
| D9S59[3] | AAGGGAATTCATCCCCTGCT (SEQ ID NO: 7) |
| | TTACACTATACCAAGACTCC (SEQ ID NO: 8) |
| ASS[3] | GGTTGGCCTAAGAAAACCAT (SEQ ID NO: 9) |
| | TGGGGAGCTATAAAAATGAC (SEQ ID NO: 10) |
| D9S66[3] | CAGACCAGGAATGCATGAAG (SEQ ID NO: 11) |
| | CACGGGCACACATGTATGC (SEQ ID NO: 12) |

*Oligonucleotide primer sequences are listed 5' to 3'.
[1]Ozelius, L., et al., Human Mol. Genet., 1(2):141 (1992)
[2]Lyall, J. E. W., et al., Nucl. Acids Res., 1991; 20(4):925
[3]Kwiatkowski, D. J., et al., Genomics, 1992; 12:229-240

Based on the linkage results obtained with HXB, GT Microsatellite analysis of chromosome 9q was performed using a panel of markers recently characterized in Kwiatkowski, D. J., et al., *Genomics*, 1992; 12:229-240; (incorporated by reference), Lyall, J. E. W., et al., *Nucl. Acid Res.*, 1992;20(4):925 (incorporated by reference), Kwiatkowski, D. J., et at., *Nucl, Acid RES.*, 1991;19:967 (incorporated by reference), and Ozelius, L., et at., *Hum. Mol. Genet*, in press (incorporated by reference). Flanking markers on both sides of HXB were tested. Markers that were located closer to the centromere than HXB (e.g., D9S59, D9S58, D9S127) gave higher lod scores, while those that were closer to the end (telomere) of the long arm (e.g., ASS) gave lower lod scores.

The highest lod score was found with D9S58 (Kwiatkowski, et al., *Nucl. Acid Res.*, supra) which has no recombinations between the marker and the disease status in all 25 familial dysautonomia families tested, and gave a lod score of 18.5 at zero distance. That means that D9S58 is located genetically at the same place as the familial dysautonomia gene with a ratio of $1:10^{18.5}$ in favor of linkage, while a ratio of $1:10^3$ is sufficient to prove linkage, and the maximal lod score possibly available with the 25 FD families is about 21 ($1:10^{21}$ in favor of linkage). All other markers that were typed, gave lower lod scores than D9S58, and all of them also show recombination events between the marker and the familial dysautonomia gene in some of the families. The current lod scores on chromosome 9 markers that show some linkage to the familial dysautonomia gene are summarized in FIG. 2. The two flanking markers that are the closest to D9S58 are D9S59 (telomeric) and D9S127 (centromeric to D9S58). The marker D9S127 is described in Lyall, et al., *Nucl. Acid Res.*, supra. These markers were mapped genetically on both sides of D9S58 on large pedigrees, at distances of 4 cM for D9S59 and about 15 cM for D9S127, and were mapped physically to the same chromosomal region as D9S58. D9S58 was mapped to a chromosomal band q31 (Kwiatkowski, et at., *Genomics.*, supra); D9S127 was mapped to the same band (Lyall, et al., *Nucl. Acid Res., supra*), and D9S59 to q31 or q32, (FIG. 1) (Kwiatkowski, et at., *Genomics.*, supra).

Thus, genetic and physical data help to map the dysautonomia gene to chromosome 9q31, at the telomeric end of the band, and to a genetic region of about 20 cM around D9S58, that correlates to about 20 million nucleotides. Although D9S58 shows complete cosegregation with the familial dysautonomia gene in all dysautonomia families that were checked, it is not possible at this stage of research to claim that D9S58 is located on top of the gene. More markers flanking D9S58 at smaller genetic distances need to be found and tested in order to locate the familial dysautonomia gene in a region small enough that will provide higher quality genetic tests for familial dysautonomia families (a region of 1-5 million nucleotides), and to specifically find the mutated gene. Narrowing down the region in which the gene is located will lead to sequencing of the familial dysautonomia gene as well as cloning thereof. Further genetic analysis employing, for example, new polymorphisms flanking D9S58 as well as the use of cosmids, YAC clones or mixtures thereof, can be employed in the narrowing down process. The next step in narrowing down will include cloning of the chromosomal region 9q31 including proximal and distal markers in a contig formed by overlapping cosmids and yeast artificial chromosomes (YACS). Subsequent subcloning in cosmids, plasmids or phages will generate additional probes for more detailed mapping.

The next step of cloning the gene will involve exon trapping, screening of cDNA libraries, Northern blots or rt PCR (reverse transcriptase PCR), of autopsy tissues from affected and unaffected individuals, direct sequencing of exons or testing axoms by SSCP (single strand conformation polymorphism), RNase protection or chemical cleavage.

Flanking markers on both sides of the familial dysautonomia gene combined with D9S58, or a number of well-positioned markers that cover the chromosomal region (q31) carrying the disease gene, can give a high probability of affected or non-affected chromosomes in the range of 80-90% accuracy, depending on the informativeness of the markers used and their distance from the disease gene. Using the current markers linked to familial dysautonomia and assuming closer flanking markers will be identified, (using the above methods) a genetic test for families with familial dysautonomia-affected member will be for both prenatal diagnosis and carrier test in healthy siblings. In the future, subsequent delineation of closely linked markers which may show strong disequilibrium with the disorder, or identification of the defective gene, could allow screening of the entire at-risk population to identify carriers, and potentially reduce the incidence of new cases of familial dysautonomia.

We claim:

1. A method for detecting the presence in a subject of a polymorphism linked to a gene associated with familial dysautonomia which comprises:
    analyzing human chromosome 9 of the subject and detecting the presence of a polymorphism located between HXB and D9S109 inclusive and linked to the gene associated with familial dysautonomia and wherein the presence of the polymorphism is indicative of carriers of a gene associated with familial dysautonomia.

2. The method according to claim 1, wherein the polymorphism is located on the q31 band of the long arm of human chromosome 9.

3. The method according to claim 1, wherein the polymorphism is selected from the group consisting of D9S58, D9S59, D9S127 and HXB.

4. The method according to claim 1, wherein the polymorphism is located about 20 cM around D9S58.

5. The method according to claim 4, wherein the polymorphism is located about 10 cM around D9S58.

6. The method according to claim 5, wherein the polymorphism is D9S58.

7. The method according to claim 1, wherein the polymorphism is located about 20 cM around D9S127.

8. The method according to claim 7, wherein the polymorphism is located about 10 cM around D9S127.

9. The method according to claim 8, wherein the polymorphism is D9S127.

10. The method according to claim 1, wherein the polymorphism is located on the chromosome between a D9S58 and D9S127.

11. The method according to claim 1, wherein the analyzing is carried out by:
    (a) amplifying the polymorphism;
    (b) separating the amplified polymorphism to generate a polymorphism pattern;
    (c) correlating the presence or absence of the polymorphism with the respective presence or absence of the gene associated with familial dysautonomia by comparing a corresponding polymorphism pattern for family members showing segregation between the familial dysautonomia gene and the polymorphism.

12. The method according to claim 11,, wherein the polymorphism is detected by autoradiography.

13. The method according to claim 11, wherein the polymorphism pattern of the subject is compared to the corresponding polymorphism pattern for each parent of the subject which are unaffected by familial dysautonomia disease and a family member affected by familial dysautonomia disease.

14. A method for detecting the presence of polymorphisms linked to a gene associated with familial dysautonomia in a subject, comprising:
    (a) detecting a maternal polymorphism linked to the gene associated with familial dysautonomia;
    (b) detecting a paternal polymorphism linked to the gene associated with familial dysautonomia;
    (c) typing the subject to determine the maternal polymorphism and paternal polymorphism;
    (d) linking the distribution of the maternal polymorphism and paternal polymorphism with familial dysautonomia; and
    (e) determining if the subject has the polymorphism located on the long arm of human chromosome 9 between HXB and D9S109, inclusive, linked to a gene associated with familial dysautonomia.

15. A method for detecting the presence of polymorphisms linked to a gene associated with familial dysautonomia in a subject comprising typing blood relatives of a subject for a polymorphism located on the long arm of human chromosome 9 located between HXB and D9S109, inclusive, and linked to the gene associated with familial dysautonomia; and analyzing DNA from the subject and detecting the presence of the polymorphism linked to the gene associated with familial dysautonomia.

16. The method according to claim 15, wherein the polymorphism is located within 20 cM of D9S58.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( i i i ) HYPOTHETICAL: No ( i v ) ORIGINAL SOURCE:
        ( A ) ORGANISM: HUMAN
        ( B ) STRAIN:
        ( C ) INDIVIDUAL ISOLATE:

-continued (D) DEVELOPMENTAL STAGE:
              (E) HAPLOTYPE:
              (F) TISSUE TYPE:
              (G) CELL TYPE:
              (H) CELL LINE:
              (I) ORGANELLE:

(ix) FEATURE:
              (A) NAME/KEY: PRIMER SEQUENCE OF HXB LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: OZELIUS, L.; SCHUBACK, D.E.; STEFANSSON, K.,
                     SLAUGENHAUPT, S.; GUSELLA, J.F.; BREAKEFIELD, X.O.
              (B) TITLE: DINUCLEOTIDE REPEAT POLYMORPHISM FOR THE
                     HEXABRACHION
                     GENE (HXB) ON CHROMOSOME 9q32-34
              (C) JOURNAL: HUMAN MOLECULAR GENETICS
              (D) VOLUME: 1
              (E) ISSUE: 2
              (F) PAGES: 141
              (G) DATE: 1992
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 1:

ATAGCCAAAG AGAGGTGCCC                                                              20

(2) INFORMATION FOR SEQ ID NO: 2:

(i) SEQUENCE CHARACTERISTICS:
              (A) LENGTH: 20
              (B) TYPE: NUCLEIC ACID
              (C) STRANDEDNESS: SINGLE
              (D) TOPOLOGY: UNKNOWN (ii) MOLECULE TYPE: OLIGONUCLEOTIDE (iii) HYPOTHETICAL: No (iv) ORIGINAL SOURCE:
              (A) ORGANISM: HUMAN
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(ix) FEATURE:
              (A) NAME/KEY: PRIMER SEQUENCE OF HXB LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: OZELIUS, L.; SCHUBACK, D.E.; STEFANSSON, K.,
                     SLAUGENHAUPT, S.; GUSELLA, J.F.; BREAKEFIELD, X.O.
              (B) TITLE: DINUCLEOTIDE REPEAT POLYMORPHISM FOR THE HEXABRACHI
                     GENE (HXB) ON CHROMOSOME 9q32-34
              (C) JOURNAL: HUMAN MOLECULAR GENETICS
              (D) VOLUME: 1
              (E) ISSUE: 2
              (F) PAGES: 141
              (G) DATE: 1992
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 2:

AGAGCCCTTC TGTCTTTTCC                                                              20

( 2 ) INFORMATION FOR SEQ ID NO: 3:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( i i i ) HYPOTHETICAL: No ( i v ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: PRIMER SEQUENCE OF D9S127 LOCUS
        ( B ) LOCATION: 9q22.1-9q32 of chromosome 9
        ( C ) IDENTIFICATION METHOD:
        ( D ) OTHER INFORMATION:

( x ) PUBLICATION INFORMATION:
        ( A ) AUTHORS: LYALL, J.E.W.; FURLONG, R.A.; YUILLE, M.A.R.;
            GOUDIE, D.R.; LEVERSHA, M.A., AFFARA,N.A., FERGUSON-
            SMITH,M.A.
        ( B ) TITLE: A DINUCLEOTIDE REPEAT POLYMORPHISM AT THE D9S127
            LOCUS
        ( C ) JOURNAL: NUCLEIC ACIDS RESEARCH
        ( D ) VOLUME:20
        ( E ) ISSUE:4
        ( F ) PAGES: 925
        ( G ) DATE: 1991
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 3:

```
CCCTCAAAAT TGCTGTCTAT                                                    20
```

( 2 ) INFORMATION FOR SEQ ID NO: 4:

( i ) SEQUENCE CHARACTERISTICS:
        ( A ) LENGTH: 23
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( i i i ) HYPOTHETICAL: No ( i v ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: PRIMER SEQUENCE OF D9S127 LOCUS
        ( B ) LOCATION: 9q22.1-9q32 OF CHROMOSOME 9
        ( C ) IDENTIFICATION METHOD:
        ( D ) OTHER INFORMATION:

( x ) PUBLICATION INFORMATION:
        ( A ) AUTHORS: LYALL, J.E.W.; FURLONG, R.A.; YUILLE, M.A.R.;

GOUDIE, D.R.; LEVERSHA, M.A., AFFARA,N.A., FERGUSON-
SMITH,M.A.
(B) TITLE: A DINUCLEOTIDE REPEAT POLYMORPHISM AT THE D9S127
LOCUS
(C) JOURNAL: NUCLEIC ACIDS RESEARCH
(D) VOLUME:20
(E) ISSUE:4
(F) PAGES: 925
(G) DATE: 1991
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 4:

AGATTGATTG ATACAAGGAT TTG 23

(2) INFORMATION FOR SEQ ID NO: 5:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (ii) MOLECULE TYPE: OLIGONUCLEOTIDE (iii) HYPOTHETICAL: No (iv) ORIGINAL SOURCE:
(A) ORGANISM: HUMAN
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY:PRIMER SEQUENCE FOR D9S58 LOCUS
(B) LOCATION: CHROMOSOME 9
(C) IDENTIFICATION METHOD:
(D) OTHER INFORMATION:

(x) PUBLICATION INFORMATION:
(A) AUTHORS: KWIATKOWSKI, DAVID J.; HENSKE, ELIZABETH P.;
WEIMER, KIM; OZELIUS, LAURIE; GUSELLA, JAMES J.; HAINES,
JONATHAN
(B) TITLE: CONSTRUCTION OF A GT POLYMORPHISM MAP OF HUMAN 9Q
(C) JOURNAL: GENOMICS
(D) VOLUME:12
(E) ISSUE:
(F) PAGES: 229-240
(G) DATE: 1992
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 5:

CCTGAGTAGC CGGGACTATA 20

(2) INFORMATION FOR SEQ ID NO: 6:

(i) SEQUENCE CHARACTERISTICS:
(A) LENGTH: 21
(B) TYPE: NUCLEIC ACID
(C) STRANDEDNESS: SINGLE
(D) TOPOLOGY: UNKNOWN (ii) MOLECULE TYPE: OLIGONUCLEOTIDE (iii) HYPOTHETICAL: No (iv) ORIGINAL SOURCE:
(A) ORGANISM: HUMAN -continued ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( i x ) FEATURE:
                    ( A ) NAME/KEY: PRIMER SEQUENCE OF D9S58 LOCUS
                    ( B ) LOCATION: CHROMOSOME 9
                    ( C ) IDENTIFICATION METHOD:
                    ( D ) OTHER INFORMATION:

( x ) PUBLICATION INFORMATION:
                    ( A ) AUTHORS: KWIATKOWSKI, DAVID J.; HENSKE, ELIZABETH P.;
                            WEIMER, KIM; OZELIUS, LAURIE; GUSELLA, JAMES J.; HAINES,
                            JONATHAN
                    ( B ) TITLE: CONSTRUCTION OF A GT POLYMORPHISM MAP OF HUMAN 9Q
                    ( C ) JOURNAL: GENOMICS
                    ( D ) VOLUME:12
                    ( E ) ISSUE:
                    ( F ) PAGES: 229-240
                    ( G ) DATE: 1992
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO: 6:

TAGGCAACAC ATCAAGATCC T                                                                                            2 1

( 2 ) INFORMATION FOR SEQ ID NO: 7:

( i ) SEQUENCE CHARACTERISTICS:
                    ( A ) LENGTH: 20
                    ( B ) TYPE: NUCLEIC ACID
                    ( C ) STRANDEDNESS: SINGLE
                    ( D ) TOPOLOGY: UNKNOWN ( i i ) MOLECULE TYPE: OLIGONUCLEOTIDE ( i i i ) HYPOTHETICAL: No ( i v ) ORIGINAL SOURCE:
                    ( A ) ORGANISM: HUMAN
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( i x ) FEATURE:
                    ( A ) NAME/KEY: PRIMER SEQUENCE OF D9S59 LOCUS
                    ( B ) LOCATION: CHROMOSOME 9
                    ( C ) IDENTIFICATION METHOD:
                    ( D ) OTHER INFORMATION:

( x ) PUBLICATION INFORMATION:
                    ( A ) AUTHORS: KWIATKOWSKI, DAVID J.; HENSKE, ELIZABETH P.;
                            WEIMER, KIM; OZELIUS, LAURIE; GUSELLA, JAMES J.; HAINES,
                            JONATHAN
                    ( B ) TITLE: CONSTRUCTION OF A GT POLYMORPHISM MAP OF HUMAN 9Q
                    ( C ) JOURNAL: GENOMICS
                    ( D ) VOLUME:12
                    ( E ) ISSUE:
                    ( F ) PAGES: 229-240
                    ( G ) DATE: 1992
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO: 7:

AAGGGAATTC ATCCCCTGCT                                                                                              2 0

( 2 ) INFORMATION FOR SEQ ID NO: 8:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( i i i ) HYPOTHETICAL: No ( i v ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: PRIMER SEQUENCE OF D9S59 LOCUS
        ( B ) LOCATION: CHROMOSOME 9
        ( C ) IDENTIFICATION METHOD:
        ( D ) OTHER INFORMATION:

( x ) PUBLICATION INFORMATION:
        ( A ) AUTHORS: KWIATKOWSKI, DAVID J.; HENSKE, ELIZABETH P.;
            WEIMER, KIM; OZELIUS, LAURIE; GUSELLA, JAMES J.; HAINES,
            JONATHAN
        ( B ) TITLE: CONSTRUCTION OF A GT POLYMORPHISM MAP OF HUMAN 9Q
        ( C ) JOURNAL: GENOMICS
        ( D ) VOLUME:12
        ( E ) ISSUE:
        ( F ) PAGES: 229-240
        ( G ) DATE: 1992
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 8:

TTACACTATA CCAAGACTCC                                        20

( 2 ) INFORMATION FOR SEQ ID NO: 9:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( i i i ) HYPOTHETICAL: No ( i v ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: PRIMER SEQUENCE OF ASS LOCUS
        ( B ) LOCATION: CHROMOSOME 9
        ( C ) IDENTIFICATION METHOD:
        ( D ) OTHER INFORMATION:

( x ) PUBLICATION INFORMATION:
        ( A ) AUTHORS: KWIATKOWSKI, DAVID J.; HENSKE, ELIZABETH P.;

WEIMER, KIM; OZELIUS, LAURIE; GUSELLA, JAMES J.; HAINES,
JONATHAN
  (B) TITLE: CONSTRUCTION OF A GT POLYMORPHISM MAP OF HUMAN 9Q
  (C) JOURNAL: GENOMICS
  (D) VOLUME:12
  (E) ISSUE:
  (F) PAGES: 229-240
  (G) DATE: 1992
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO: 9:

GGTTGGCCTA AGAAAACCAT 20

(2) INFORMATION FOR SEQ ID NO: 10:

(i) SEQUENCE CHARACTERISTICS:
    (A) LENGTH: 20
    (B) TYPE: NUCLEIC ACID
    (C) STRANDEDNESS: SINGLE
    (D) TOPOLOGY: UNKNOWN (ii) MOLECULE TYPE: OLIGONUCLEOTIDE (iii) HYPOTHETICAL: No (iv) ORIGINAL SOURCE:
    (A) ORGANISM: HUMAN
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(ix) FEATURE:
    (A) NAME/KEY: PRIMER SEQUENCE OF ASS LOCUS
    (B) LOCATION: CHROMOSOME 9
    (C) IDENTIFICATION METHOD:
    (D) OTHER INFORMATION:

(x) PUBLICATION INFORMATION:
    (A) AUTHORS: KWIATKOWSKI, DAVID J.; HENSKE, ELIZABETH P.;
        WEIMER, KIM; OZELIUS, LAURIE; GUSELLA, JAMES J.; HAINES,
        JONATHAN
    (B) TITLE: CONSTRUCTION OF A GT POLYMORPHISM MAP OF HUMAN 9Q
    (C) JOURNAL: GENOMICS
    (D) VOLUME:12
    (E) ISSUE:
    (F) PAGES: 229-240
    (G) DATE: 1992
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 10:

TGGGGAGCTA TAAAAATGAC 20

(2) INFORMATION FOR SEQ ID NO: 11:

(i) SEQUENCE CHARACTERISTICS:
    (A) LENGTH: 20
    (B) TYPE: NUCLEIC ACID
    (C) STRANDEDNESS: SINGLE
    (D) TOPOLOGY: UNKNOWN (ii) MOLECULE TYPE: OLIGONUCLEOTIDE (iii) HYPOTHETICAL: No (iv) ORIGINAL SOURCE:
    (A) ORGANISM: HUMAN
    (B) STRAIN:

(C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(ix) FEATURE:
                (A) NAME/KEY: PRIMER SEQUENCE OF D9S66 LOCUS
                (B) LOCATION: CHROMOSOME 9
                (C) IDENTIFICATION METHOD:
                (D) OTHER INFORMATION:

(x) PUBLICATION INFORMATION:
                (A) AUTHORS: KWIATKOWSKI, DAVID J.; HENSKE, ELIZABETH P.;
                        WEIMER, KIM; OZELIUS, LAURIE; GUSELLA, JAMES J.; HAINES,
                        JONATHAN
                (B) TITLE: CONSTRUCTION OF A GT POLYMORPHISM MAP OF HUMAN 9Q
                (C) JOURNAL: GENOMICS
                (D) VOLUME:12
                (E) ISSUE:
                (F) PAGES: 229-240
                (G) DATE: 1992
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 11:

CAGACCAGGA ATGCATGAAG                                                                           20

(2) INFORMATION FOR SEQ ID NO: 12:

(i) SEQUENCE CHARACTERISTICS:
                (A) LENGTH: 19
                (B) TYPE: NUCLEIC ACID
                (C) STRANDEDNESS: SINGLE
                (D) TOPOLOGY: UNKNOWN (ii) MOLECULE TYPE: OLIGONUCLEOTIDE (iii) HYPOTHETICAL: No (iv) ORIGINAL SOURCE:
                (A) ORGANISM: HUMAN
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(ix) FEATURE:
                (A) NAME/KEY: PRIMER SEQUENCE OF D9S66 LOCUS
                (B) LOCATION: CHROMOSOME 9
                (C) IDENTIFICATION METHOD:
                (D) OTHER INFORMATION:

(x) PUBLICATION INFORMATION:
                (A) AUTHORS: KWIATKOWSKI, DAVID J.; HENSKE, ELIZABETH P.;
                        WEIMER, KIM; OZELIUS, LAURIE; GUSELLA, JAMES J.; HAINES,
                        JONATHAN
                (B) TITLE: CONSTRUCTION OF A GT POLYMORPHISM MAP OF HUMAN 9Q
                (C) JOURNAL: GENOMICS
                (D) VOLUME:12
                (E) ISSUE:
                (F) PAGES: 229-240
                (G) DATE: 1992
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 12:

CACGGGCACA CATGTATGC                                                                            19